United States Patent
Ohtsuka et al.

(10) Patent No.: US 11,377,407 B2
(45) Date of Patent: Jul. 5, 2022

(54) METHOD FOR PRODUCING DIFLUOROMETHYLENE COMPOUND

(71) Applicant: DAIKIN INDUSTRIES, LTD., Osaka (JP)

(72) Inventors: Tatsuya Ohtsuka, Osaka (JP); Yoshichika Kuroki, Osaka (JP); Atsushi Shirai, Osaka (JP); Moe Hosokawa, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/048,760

(22) PCT Filed: Apr. 25, 2019

(86) PCT No.: PCT/JP2019/017575
§ 371 (c)(1),
(2) Date: Oct. 19, 2020

(87) PCT Pub. No.: WO2019/208682
PCT Pub. Date: Oct. 31, 2019

(65) Prior Publication Data
US 2021/0363077 A1 Nov. 25, 2021

(30) Foreign Application Priority Data
Apr. 25, 2018 (JP) .............. JP2018-084473

(51) Int. Cl.
*C07C 17/18* (2006.01)
*C07C 17/32* (2006.01)

(52) U.S. Cl.
CPC .............. *C07C 17/32* (2013.01); *C07C 17/18* (2013.01); *C07C 2601/16* (2017.05)

(58) Field of Classification Search
CPC .................................................. C07C 17/18
See application file for complete search history.

(56) References Cited

U.S. PATENT DOCUMENTS 7,265,247 B1 9/2007 Umemoto et al.

FOREIGN PATENT DOCUMENTS

WO  WO-2018123890 A1 * 7/2018 ............. C07C 17/18

OTHER PUBLICATIONS

English translation international publication WO2018123890A1, Jul. 2018, pp. 1-24 (Year: 2018).*
Yoneda, N. et al. "Novel Fluorination Reagent: IF5 / Et3N-3HF" Chemistry Letters 2001, pp. 222-223 (Year: 2001).*
Hara, S. et al. "Direct Fluorination of Adamantanes with Iodine Pentafluoride" Synthesis, 2008(16), 2510-2512 (Year: 2008).*
Hugenberg et al., "Fluoro-Pummerer rearrangement and analogous reactions", Journal of Fluorine Chemistry, 2012, vol. 143, pp. 238-262.
Inoue et al., "Trifluorination of sulfides and dithioketals using $IF_5$-pyridine-HF", Journal of Fluorine Chemistry, 2016, vol. 184, pp. 22-27.
International Search Report dated Jul. 23, 2019 in International (PCT) Application No. PCT/JP2019/017575.
Hasek et al., "The Chemistry of Sulfur Tetrafluoride. II. The Fluorination of Organic Carbonyl Compounds", Journal of the American Chemical Society, 1960, vol. 82, No. 3, pp. 543-551.
Middleton et al., "New Fluorinating Reagents. Dialkylaminosulfur Fluorides", The Journal of Organic Chemistry, 1975, vol. 40, No. 5, pp. 574-578.
Lal et al., "Bis(2-methoxyethyl)aminosulfur trifluoride: a new broad-spectrum deoxofluorinating agent with enhanced thermal stability", Chemical Communications, 1999, pp. 215-216.
Extended European Search Report dated Mar. 18, 2022 in corresponding European Patent Application No. 19792724.7.

* cited by examiner

*Primary Examiner* — Medhanit W Bahta
(74) *Attorney, Agent, or Firm* — Wenderoth, Lind & Ponack, L.L.P.

(57) ABSTRACT

The problem to be solved by the present invention is to provide a novel method for producing a difluoromethylene compound, in particular, a simple method for producing a difluoromethylene compound. This problem is solved by a method for producing a difluoromethylene compound (I) containing at least one —$CF_2$— moiety, the method comprising step A of allowing $IF_5$ and a disulfide compound (III) of the formula: $R^4$—S—S—$R^4$ (wherein $R^4$, in each occurrence, independently represents aryl optionally having at least one substituent or alkyl optionally having at least one substituent) to act on a carbonyl compound (II) containing at least one —C(O)— moiety.

10 Claims, No Drawings

METHOD FOR PRODUCING DIFLUOROMETHYLENE COMPOUND

TECHNICAL FIELD

The present invention relates to a method for producing a difluoromethylene compound.

BACKGROUND ART

Compounds having a difluoromethylene skeleton (i.e., difluoromethylene compounds) are useful as a liquid crystal material, a medicinal drug, an intermediate thereof, etc. Various production methods for the compounds have been studied; and of such methods, the deoxyfluorination of carbonyl compounds is a useful reaction. Fluorinating agents known to be suitable for such a reaction include sulfur tetrafluoride ($SF_4$), N,N-diethylaminosulfur trifluoride (DAST), bis(methoxymethyl)aminosulfur trifluoride (Deoxo-Fluor, trade name), substituted phenylsulfur trifluoride (Fluolead, trade name), and the like.

However, $SF_4$, which is highly toxic and is in the form of a gas, is not easily handled and is not easily obtained. DAST and Deoxo-Fluor are liquids that have low thermal stability, and that generate a very large amount of thermal energy when decomposed. In particular, DAST is explosive, and requires caution when handled. Although Fluolead is highly stable, there is a problem in that sulfur compounds produced as a byproduct by the decomposition of a fluorinating agent are not easily separated from the reaction product.

CITATION LIST

Patent Literature

PTL 1: U.S. Pat. No. 7,265,247

Non-Patent Literature

NPL 1: J. Am. Chem. Soc., 82, 543 (1960)
NPL 2: J. Org. Chem., 40, 574 (1975)
NPL 3: Chemical Communications 215 (1999)

SUMMARY OF INVENTION

Technical Problem

An object of the present invention is to provide a novel method for producing a difluoromethylene compound; in particular, a simple method for producing a difluoromethylene compound.

Solution to Problem

As a result of extensive research, the present inventors found that a difluoromethylene compound (I) containing at least one —$CF_2$— moiety is obtained by a production method comprising step A of allowing $IF_5$ and at least one disulfide compound (III) represented by the formula: $R^4$—S—S—$R^4$ (wherein $R^4$, in each occurrence, independently represents aryl optionally having at least one substituent or alkyl optionally having at least one substituent) to act on a carbonyl compound (II) containing at least one —C(O)— moiety. In other words, the present inventors found that the above problems can be solved. The present invention has thus been completed.

The present invention encompasses the following embodiments.

Item 1.

A method for producing a difluoromethylene compound (I) containing at least one —$CF_2$— moiety, the method comprising step A of allowing $IF_5$ and a disulfide compound (III) of the formula: $R^4$—S—S—$R^4$, wherein $R^4$, in each occurrence, independently represents aryl optionally having at least one substituent or alkyl optionally having at least one substituent, to act on a carbonyl compound (II) containing at least one —C(O)— moiety.

Item 2.

The production method according to Item 1, wherein the difluoromethylene compound (I) is a difluoromethylene compound represented by formula (1):

$$R^{11}-C_2-R^{12} \qquad (1),$$

wherein $R^{11}$ and $R^{12}$ are identical or different, and each represents (a) an organic group optionally containing at least one —$CF_2$— moiety or (b) fluorine, and the carbonyl compound (II) is a carbonyl compound represented by formula (2):

$$R^{21}-C(O)-R^{22} \qquad (2),$$

wherein $R^{21}$ and $R^{22}$ are identical or different, and each represents (a) hydrogen, (b) hydroxyl, or (c) an organic group optionally containing at least one —CO— moiety, or $R^{21}$ and $R^{22}$, taken together with the adjacent —C(O)— moiety, may form a ring, with the proviso that (i) neither $R^{11}$ nor $R^{12}$ is hydroxyl, and (ii) neither $R^{11}$ nor $R^{12}$, and neither $R^{21}$ nor $R^{22}$, is an organic group bonded via —O—.

Item 3.

The production method according to Item 1, wherein the difluoromethylene compound (I) is a difluoromethylene compound represented by formula (1):

$$R^{11}-C_2-R^{12} \qquad (1),$$

wherein $R^{11}$ represents $R^{21}$ or fluorine, $R^{12}$ represents $R^{22}$ or fluorine, $R^{21}$ and $R^{22}$ are identical or different, and each represents (a) hydrogen, (b) hydroxyl, or (c) an organic group, or $R^{21}$ and $R^{22}$, taken together with the adjacent —$CF_2$— moiety, may form a ring, with the proviso that (i) neither $R^{11}$ nor $R^{12}$ is hydroxyl, and (ii) neither $R^{11}$ nor $R^{12}$, and neither $R^{21}$ nor $R^{22}$, is an organic group bonded via —O—, and the carbonyl compound (II) is a carbonyl compound represented by formula (2):

$$R^{21}-C(O)-R^{22} \qquad (2),$$

wherein
the symbols in the formula are as defined above.
Item 4.

The production method according to any one of Items 1 to 3, wherein at least one member selected from the group consisting of acids, salts, and additives is allowed to act together with $IF_5$.
Item 5.

The production method according to any one of Items 1 to 3, wherein an acid and a base are allowed to act together with $IF_5$.
Item 6.

The production method according to Item 4 or 5, wherein the acid is hydrogen fluoride.
Item 7.

The production method according to Item 5 or 6, wherein the base is a 5-membered monocyclic nitrogen-containing aromatic heterocyclic compound optionally substituted with one or more alkyl groups.
Item 8.

The production method according to any one of Items 1 to 7, wherein $R^A$, in each occurrence, independently represents aryl optionally having at least one substituent.

Advantageous Effects of Invention

The present invention provides a novel method for producing a difluoromethylene compound; in particular, a simple, efficient method for producing a difluoromethylene compound.

DESCRIPTION OF EMBODIMENTS

1. Terms

The symbols and the abbreviations in this specification are to be interpreted as having the general meanings in the related technical field to which the present invention pertains, according to the context of this specification, unless otherwise specified.

In this specification, the term "comprise" or "contain" is intended to encompass the meanings of "consist essentially of" and "consist of."

The steps, treatments, or operations in this specification can be performed at room temperature, unless otherwise specified.

In this specification, room temperature refers to a temperature of 10 to 40° C.

In this specification, the term "$C_n$-$C_m$" (wherein n and m are numbers) indicates that the carbon number is n or more and m or less, as would usually be understood by a person skilled in the art.

In this specification, examples of "non-aromatic hydrocarbon ring" include $C_3$-$C_8$ non-aromatic hydrocarbon rings. Specific examples include:

(1) $C_3$-$C_8$ cycloalkanes, such as cyclopropane, cyclobutane, cyclopentane, cyclohexane, cycloheptane, and cyclooctane;

(2) $C_5$-$C_8$ cycloalkenes, such as cyclopentene, cyclohexene, cycloheptene, and cyclooctene;

(3) $C_5$-$C_8$ cycloalkadienes, such as cyclopentadiene, cyclohexadiene, cycloheptadiene, and cyclooctadiene;

(4) $C_5$-$C_8$ bridged-ring hydrocarbons, such as bicyclo[2.1.0]pentane, bicyclo[2.2.1]heptane, bicyclo[3.2.1]octane, bicyclo[2.2.1]hept-2-ene, and tricyclo[2.2.1.0]heptane; and the like.

In this specification, examples of "non-aromatic heterocycle" include 3- to 8-membered non-aromatic heterocycles and the like. Specific examples include oxirane, azetidine, oxetane, thietane, pyrrolidine, dihydrofuran, tetrahydrofuran, tetrahydrothiophene, imidazolidine, oxazolidine, isoxazoline, piperidine, dihydropyran, tetrahydropyran, tetrahydrothiopyran, morpholine, thiomorpholine, piperazine, dihydrooxazine, tetrahydrooxazine, dihydropyrimidine, tetrahydropyrimidine, azepane, oxepane, thiepane, oxazepane, thiazepane, azocane, oxocane, thiocane, oxazocane, thiazocane, and the like.

In this specification, the term "organic group" refers to a group containing at least one carbon atom, or a group formed by removing one hydrogen atom from an organic compound.

Examples of the "organic group" include hydrocarbon optionally having at least one substituent, non-aromatic heterocyclic group optionally having at least one substituent, heteroaryl optionally having at least one substituent,
cyano,
aldehyde,
RO—,
RCO—,
$RSO_2$—,
ROCO—, and
$ROSO_2$—
(in these formulas, Rs are each independently hydrocarbon optionally having at least one substituent, non-aromatic heterocyclic group optionally having at least one substituent, or
heteroaryl optionally having at least one substituent).

In this specification, examples of "hydrocarbon" include alkyl, alkenyl, alkynyl, cycloalkyl, cycloalkenyl, cycloalkadienyl, aryl, aralkyl, and groups of combinations thereof.

In this specification, "(cyclo)alkyl" refers to alkyl and/or cycloalkyl.

In this specification, examples of "alkyl" include linear or branched $C_1$-$C_{10}$ alkyl, such as methyl (in this specification, sometimes referred to as "Me"), ethyl, propyl, isopropyl, butyl, isobutyl, sec-butyl, tert-butyl, pentyl, isopentyl, neopentyl, hexyl, heptyl, octyl, nonyl, and decyl, unless otherwise specified.

In this specification, examples of "alkenyl" include linear or branched $C_2$-$C_{10}$ alkenyl, such as vinyl, 1-propen-1-yl, 2-propen-1-yl, isopropenyl, 2-buten-1-yl, 4-penten-1-yl, and 5-hexen-1-yl, unless otherwise specified.

In this specification, examples of "alkynyl" include linear or branched $C_2$-$C_{10}$ alkynyl, such as ethynyl, 1-propyn-1-yl, 2-propyn-1-yl, 4-pentyn-1-yl, and 5-hexyne-1-yl, unless otherwise specified.

In this specification, examples of "cycloalkyl" include $C_3$-$C_7$ cycloalkyl, such as cyclopropyl, cyclobutyl, cyclopentyl, cyclohexyl, and cycloheptyl, unless otherwise specified.

In this specification, examples of "cycloalkenyl" include $C_3$-$C_7$ cycloalkenyl, such as cyclopropenyl, cyclobutenyl, cyclopentenyl, cyclohexenyl, and cycloheptenyl, unless otherwise specified.

In this specification, examples of "cycloalkadienyl" include $C_4$-$C_{10}$ cycloalkadienyl, such as cyclobutadienyl, cyclopentadienyl, cyclohexadienyl, cycloheptadienyl, cyclooctadienyl, cyclononadienyl, and cyclodecadienyl, unless otherwise specified.

In this specification, "aryl" may be monocyclic, bicyclic, tricyclic, or tetracyclic, unless otherwise specified.

In this specification, "aryl" may be $C_6$-$C_{18}$ aryl, unless otherwise specified.

In this specification, examples of "aryl" include phenyl (in this specification, sometimes referred to as "Ph"), 1-naphthyl, 2-naphthyl, 2-biphenyl, 3-biphenyl, 4-biphenyl, and 2-anthryl, unless otherwise specified.

In this specification, examples of "aralkyl" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, and 4-biphenylylmethyl, unless otherwise specified.

In this specification, "non-aromatic heterocyclic group" may be monocyclic, bicyclic, tricyclic, or tetracyclic, unless otherwise specified.

In this specification, "non-aromatic heterocyclic group" may be, for example, a non-aromatic heterocyclic group containing, in addition to carbon, 1 to 4 heteroatoms selected from oxygen, sulfur, and nitrogen as a ring-constituting atom or ring-constituting atoms, unless otherwise specified.

In this specification, "non-aromatic heterocyclic group" may be saturated or unsaturated, unless otherwise specified.

In this specification, examples of "non-aromatic heterocyclic group" include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, and the like, unless otherwise specified.

In this specification, examples of "heteroaryl" include 5- or 6-membered monocyclic aromatic heterocyclic groups, 5- to 10-membered aromatic fused heterocyclic groups, and the like, unless otherwise specified.

In this specification, examples of "5- or 6-membered monocyclic aromatic heterocyclic group" include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), pyrazinyl, and the like, unless otherwise specified.

In this specification, examples of "5- to 10-membered aromatic fused heterocyclic group" include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), and the like, unless otherwise specified.

In this specification, examples of "halogen atom" include fluorine, chlorine, bromine, and iodine, unless otherwise specified.

In this specification, examples of the term "halogenated" can include the meanings of chlorinated, brominated, and iodinated, unless otherwise specified.

2. Production Method

The method of the present invention for producing a difluoromethylene compound (I) containing at least one —$CF_2$— moiety (in this specification, sometimes simply referred to as "the difluoromethylene compound (I)") comprises step A of allowing $IF_5$ and a disulfide compound (III) represented by the formula: $R^A$—S—S—$R^A$ (wherein $R^A$, in each occurrence, independently represents aryl optionally having at least one substituent or alkyl optionally having at least one substituent) to act on a carbonyl compound (II) containing a —C(O)— moiety (in this specification, sometimes simply referred to as "the carbonyl compound (II)").

Examples of the substituents of the "aryl optionally having at least one substituent" represented by $R^A$ include hydroxyl and organic groups.

The number of the substituents may be within a range of one to the maximum replaceable number (e.g., one, two, three, four, five, or six).

Preferable examples of the "substituents" of the "aryl optionally having at least one substituent" represented by $R^A$ include hydroxyl,
halogen atoms,
primary, secondary, or tertiary $C_2$-$C_8$ alkyl, and
primary, secondary, or tertiary $C_2$-$C_8$ alkyl containing at least one ether bond internally or at the end.

More preferable example of the "substituents" of the "alkyl optionally having at least one substituent" represented by $R^A$ include
fluorine,
chlorine,
primary, secondary, or tertiary $C_2$-$C_4$ alkyl, and
primary, secondary, or tertiary $C_2$-$C_4$ alkyl containing at least one ether bond internally or at the end.

Just to note, the term "difluoromethylene" in the difluoromethylene compound (I) produced by the production method of the present invention refers to the —$CF_2$— moiety.

The difluoromethylene compound (I) can contain at least one —$CF_2$— moiety.

Corresponding to this, the carbonyl compound (II) can contain at least one —C(O)— moiety.

The carbonyl compound (II) used in the production method of the present invention is converted in step A into the difluoromethylene compound (I) containing a —$CF_2$— moiety.

It is preferable that a compound in which an organic group is bonded to the —C(O)— moiety via —O— (i.e., an ester compound) is excluded from the carbonyl compound (II), which is a starting material compound for the reaction.

Accordingly, it is preferable that a compound in which an organic group is bonded to the —$CF_2$— moiety via —O— is excluded from the difluoromethylene compound (I), which is the reaction product.

Just to note, the —$CF_2$— moiety in the difluoromethylene compound (I), i.e., the reaction product, may be, for example, part of a —$CF_3$ group. That is, the difluoromethylene compound may be a trifluoromethyl compound.

In regard to this, when —COOH is attached to the —C(O)— moiety in the carbonyl compound (II), the —C(O)—COOH moiety can be converted into a —$CF_3$ group in step A. Therefore, in this case, a trifluoromethyl compound is produced by the production method of the present invention.

The difluoromethylene compound (I) produced by the production method of the present invention is preferably a difluoromethylene compound represented by formula (1):

    (1)

(wherein
$R^{11}$ and $R^{12}$ are identical or different, and each represents
(a) an organic group optionally containing at least one —$CF_2$— moiety or
(b) fluorine).

Corresponding to the difluoromethylene compound (1) as a preferable difluoromethylene compound (I), the carbonyl compound (II) is preferably a carbonyl compound represented by formula (2):

    (2)

(wherein
$R^{21}$ and $R^{22}$ are identical or different and each represents
(a) hydrogen,
(b) hydroxyl, or
(c) an organic group optionally containing at least one —CO— moiety, or $R^{21}$ and $R^{22}$, taken together with the adjacent —C(O)— moiety may form a ring, with the proviso that
(i) neither $R^{11}$ nor $R^{12}$ is hydroxyl, and
(ii) neither $R^{11}$ nor $R^{12}$, and neither $R^{21}$ nor $R^{22}$, is an organic group bonded via —O—).

An example of the difluoromethylene compound (I) produced by the production method of the present invention is a difluoromethylene compound represented by formula (1):

    (1)

(wherein
$R^{11}$ represents $R^{21}$ or fluorine,
$R^{12}$ represents $R^{22}$ or fluorine,
$R^{21}$ and $R^{22}$ are identical or different and each represents
(a) hydrogen,
(b) hydroxyl, or
(c) an organic group, or
$R^{21}$ and $R^{22}$ may be attached to each other, with the proviso that
(i) neither $R^{11}$ nor $R^{12}$ is hydroxyl, and
(ii) neither $R^{11}$ nor $R^{12}$, and neither $R^{21}$ nor $R^{22}$, is an organic group bonded via —O—).

Corresponding to the one example of the difluoromethylene compound (I), examples of the carbonyl compound (II) include a carbonyl compound represented by formula (2):

    (2)

(wherein the symbols in the formula are as defined above).

$R^{11}$ in formula (1) representing the target compound corresponds to $R^{21}$ in formula (2) representing a starting material compound for the reaction, and $R^{11}$ and $R^{21}$ may be identical or different.

$R^{12}$ in formula (1) representing the target compound corresponds to $R^{22}$ in formula (2) representing a starting material compound for the reaction, and $R^{12}$ and $R^{22}$ may be identical or different.

When the organic group represented by $R^{21}$ in formula (2) above contains at least one —CO— moiety, part or all of the —CO— moieties can be converted into —$CF_2$— moieties by the reaction of step A.

When the organic group represented by $R^{22}$ in formula (2) contains at least one —CO— moiety, part or all of the —CO— moieties can be converted into —$CF_2$— moieties by the reaction of step A.

However, as is understood from the description above, in the production method according to this embodiment, when $R^{22}$ in formula (2) above is —COOH, $R^{11}$ in formula (1) may be fluorine.

Similarly, in the production method according to this embodiment, when $R^{22}$ in formula (2) above is —COOH, $R^{22}$ in formula (1) may be fluorine.

The organic group represented by $R^{11}$ is preferably hydrocarbon optionally having at least one substituent. (This hydrocarbon may contain at least one moiety selected from the group consisting of —NR—, =N—, —N=, —O—, and —S—, wherein R represents hydrogen or an organic group.)

The "hydrocarbon" in the "hydrocarbon optionally having at least one substituent" is preferably $C_1$-$C_{30}$ hydrocarbon, more preferably $C_1$-$C_{20}$ hydrocarbon, and still more preferably $C_1$-$C_{10}$ hydrocarbon.

The hydrocarbon is preferably alkyl or aryl, and more preferably $C_1$-$C_{10}$ alkyl or $C_6$-$C_{20}$ aryl.

The hydrocarbon (including alkyl and aryl) may contain at least one moiety selected from the group consisting of —NR— (wherein R represents hydrogen or an organic group), =N—, —N=, —O—, and —S—.

This moiety may be inserted between the carbon-carbon bonding of the hydrocarbon and/or inserted adjacent to the —CF$_2$— moiety in formula (1) (and corresponding to this, may be inserted adjacent to the —C(O)— moiety in formula (2)).

The organic group represented by R in the —NR— moiety is preferably hydrocarbon optionally having at least one substituent; and the hydrocarbon in the "hydrocarbon optionally having at least one substituent" is preferably C$_1$-C$_{30}$ hydrocarbon, more preferably C$_1$-C$_{20}$ hydrocarbon, and still more preferably C$_1$-C$_{10}$ hydrocarbon.

The organic group represented by R$^{12}$ is preferably hydrocarbon optionally having at least one substituent. (This hydrocarbon may contain at least one moiety selected from the group consisting of —NR—, =N—, —N=, —O—, and —S—, wherein R represents hydrogen or an organic group.)

The "hydrocarbon" in the "hydrocarbon optionally having at least one substituent" is preferably C$_1$-C$_{30}$ hydrocarbon, more preferably C$_1$-C$_{20}$ hydrocarbon, and still more preferably C$_1$-C$_{10}$ hydrocarbon.

The hydrocarbon is preferably alkyl or aryl, and more preferably C$_1$-C$_{10}$ alkyl or C$_6$-C$_{20}$ aryl.

The hydrocarbon (including alkyl and aryl) may contain at least one moiety selected from the group consisting of —NR— (wherein R represents hydrogen or an organic group), =N—, —N=, —O—, and —S—.

This moiety may be inserted between the carbon-carbon bonding of the hydrocarbon and/or inserted adjacent to the —CF$_2$— moiety in formula (1).

The organic group represented by R in R$^{12}$ is preferably hydrocarbon optionally having at least one substituent; and the hydrocarbon in the "hydrocarbon optionally having at least one substituent" is preferably C$_1$-C$_{20}$ hydrocarbon, more preferably C$_1$-C$_{10}$ hydrocarbon, and still more preferably C$_1$-C$_5$ hydrocarbon.

Just to note, as a person skilled in the art would usually understand, aryl containing at least one moiety selected from the group consisting of —NR—, =N—, —N=, —O—, and —S— may be heteroaryl.

Examples of the "substituent" in the "hydrocarbon optionally having at least one substituent" represented by R$^{11}$ or R$^{21}$ include halogen atoms, nitro, cyano, oxo, thioxo, sulfo, sulfamoyl, sulfinamoyl, and sulfenamoyl.

The numbers of the substituents in R$^{11}$ and R$^{21}$ may be the same or different, and within a range of one to the maximum replaceable number (e.g., one, two, three, four, five, or six).

It is preferable that the ring formed by R$^{11}$ and R$^{21}$, taken together with the adjacent —CF$_2$— moiety, be a 3- to 8-membered ring optionally further having at least one substituent, in addition to fluorine in the —CF$_2$— moiety.

The ring may be a monocyclic, fused, or spiro ring.

The ring may be a non-aromatic hydrocarbon ring or non-aromatic heterocycle.

Examples of the substituent include halogen atoms, nitro, cyano, oxo, thioxo, sulfo, sulfamoyl, sulfinamoyl, and sulfenamoyl.

The number of the substituents may be within a range of one to the maximum replaceable number (e.g., one, two, three, four, five, or six).

Just to note, the "organic group bonded via —O—" excluded from R$^{21}$ and R$^{22}$ is, for example, hydrocarbyloxy optionally having at least one substituent.

In step A, IF$_5$ is allowed to act on the carbonyl compound (II), which is a substrate.

It is possible to allow IF$_5$ to act on the carbonyl compound (II) directly or indirectly.

That is, IF$_5$ and the disulfide compound (III) may directly act on the carbonyl compound (II), which is a substrate, or a substance generated involving IF$_5$ and the disulfide compound (III) may act on the carbonyl compound (II).

The disulfide compound (III) is obtained, for example, by reacting R$^A$—H and S$_2$Cl$_2$.

The amount of IF$_5$ is preferably 0.2 to 20 moles, and more preferably 0.5 to 10 moles, per mol of the carbonyl compound (II), which is a substrate.

In the production method of the present invention, it is preferable to further use at least one member selected from the group consisting of acids, bases, salts, and additives, together with IF$_5$; and more preferable to use 1 to 3 members selected from the group thereof (and still more preferable to use 1 to 3 members selected from the group thereof, excluding combinations of an acid, a base, and a salt).

Examples of the "acid" include hydrogen halides (e.g., HF), hydrohalic acids, hypohalous acids, halous acids, halogen acids, and perhalogen acids (e.g., sulfuric acid, nitric acid, phosphoric acid, polyphosphoric acid, hydrogen fluoride, hydrofluoric acid, hydrochloric acid, hydrogen bromide, hydrogen iodide, hypochlorous acid, chlorous acid, chloric acid, perchloric acid, perbromic acid, periodic acid); sulfonic acids (e.g. fluorosulfonic acid, chlorosulfonic acid, methanesulfonic acid, ethanesulfonic acid, trifluoromethanesulfonic acid, difluoromethanesulfonic acid, trichloromethanesulfonic acid, perfluorobutanesulfonic acid, perfluorooctanesulfonic acid, benzenesulfonic acid, toluenesulfonic acid, nitrobenzenesulfonic acid); polymers carrying sulfonic acids (e.g., polystyrenesulfonic acid, fluorinated sulfonic acid resin (e.g., Nafion-H)); formic acid, acetic acid, propionic acid, chloroacetic acid, bromacetic acid, dichloroacetic acid, trichloroacetic acid, and mono- or polycarboxylic acids (e.g., trifluoroacetic acid, glycolic acid, lactic acid, benzoic acid, oxalic acid, succinic acid); Lewis acids and their ether complexes (e.g., SO$_3$, BF$_3$, BCl$_3$, B(OCH$_3$)$_3$, AlCl$_3$, AlBr$_3$, SbF$_3$, SbCl$_3$, SbF$_5$, PF$_3$, PFS, AsF$_3$, AsCl$_3$, AsF$_5$, TiCl$_4$, NbF$_4$, TaF$_4$); and acids formed of Lewis acids and hydrogen halides, and their ether complexes (e.g., HBF$_4$, HPF$_6$, HAsF$_6$, HSbF$_6$, HSbCl$_6$).

The acids used here may be supported by carriers.

Examples of the carriers include SiO$_2$, methylated SiO$_2$, Al$_2$O$_3$, Al$_2$O$_3$—WB, MoO$_3$, ThO$_2$, ZrO$_2$, TiO$_2$, Cr$_2$O$_3$, SiO$_2$—Al$_2$O$_3$, SiO$_2$—TiO$_2$, SiO$_2$—ZrO$_2$, TiO$_2$ZrO$_2$, Al$_2$O$_3$—B$_2$O$_3$, SiO$_2$—WO$_3$, SiO$_2$—NH$_4$F, HSO$_3$Cl—Al$_2$O$_3$, HF—NH$_4$—Y, HF—Al$_2$O$_3$, NH$_4$F—SiO$_2$—Al$_2$O$_3$, AlF$_3$—Al$_2$O$_3$, Ru—F—Al$_2$O$_3$, F—Al$_2$O$_3$, KF—Al$_2$O$_3$, AlPO$_4$, AlF$_3$, bauxite, kaolin, activated carbon, graphite, Pt-graphite, metal sulfate, metal chloride, metals (e.g., Al), alloys (e.g., Al—Mg, Ni—Mo), polymers (e.g., polystyrene, ion exchange resins), and the like.

These acids may be used alone, or in a combination of two or more.

The amount of the acid may be selected from a range from a catalytic amount to a large excess.

Specifically, the amount of the acid is preferably 0.01 moles to 100 moles, and more preferably 0.1 moles to 20 moles, per mol of the carbonyl compound (II).

The acid can also be used as a reaction solvent. In this case, the amount of the acid may be a very small amount or a large excess.

Examples of the "base" include
(i) alkali metal hydroxides or alkaline earth metal hydroxides (e.g. sodium hydroxide, potassium hydroxide, lithium hydroxide, rubidium hydroxide, cesium hydroxide, magnesium hydroxide, calcium hydroxide, barium hydroxide);
(ii) alkali metal alkoxides (e.g., sodium methoxide, sodium ethoxide, sodium butoxide, potassium methoxide, potassium ethoxide, potassium butoxide, lithium methoxide, lithium ethoxide);
(iii) alkali metal hydrides or alkaline earth metal hydrides (e.g., sodium hydride, potassium hydride, lithium hydride, calcium hydride);
(iv) alkali metals (e.g., sodium, potassium, lithium);
(v) alkaline earth metal oxides (e.g., magnesium oxide, calcium oxide); and ammonia and ammonium hydroxide salts (e.g., ammonium hydroxide, tetramethylammonium hydroxide, tetraethylammonium hydroxide, tetrabutylammonium hydroxide, octyltriethylammonium hydroxide, benzyltrimethylammonium hydroxide); and
(vi) polymer carrying ammonium hydroxide salts (e.g., Amberlite resin), and the like; and
organic bases, such as aliphatic amines (primary amines, secondary amines, tertiary amines), alicyclic amines (secondary amines, tertiary amines), aromatic amines (primary amines, secondary amines, tertiary amines), heterocyclic amines, and polymer carrying amine compounds.

Examples of aliphatic primary amines include methylamine, ethylamine, propylamine, butylamine, pentylamine, hexylamine, cyclohexylamine, and ethylenediamine.

Examples of aliphatic secondary amines include dimethylamine, diethylamine, dipropylamine, dibutylamine, dipentylamine, dihexylamine, and dicyclohexylamine. Examples of aliphatic tertiary amines include trimethylamine, triethylamine, diisopropylethylamine, and N,N,N',N'-tetramethylethylenediamine.

Examples of alicyclic secondary amines include piperidine, piperazine, pyrrolidine, and morpholine.

Examples of alicyclic tertiary amines include N-methylpiperazine, N-methylpyrrolidine, 5-diazabicyclo[4.3.0]nonan-5-ene, and 1,4-diazabicyclo[2.2.2]octane.

Examples of aromatic amines include aniline, methylaniline, dimethylaniline, N,N-dimethylaniline, haloaniline, nitroaniline, and phenylenediamine.

Examples of heterocyclic amines include piperidine, pyridine, lutidine, pyrimidine, piperazine, quinoline, and imidazol.

Examples of polymer carrying amine compounds include polyallylamine and polyvinylpyridine.

Preferable examples of the "base" include the following compounds (i) to (vi).
(i) A 5-membered monocyclic nitrogen-containing aromatic heterocyclic compound optionally substituted with one or more alkyl groups (this ring contains 1 to 3 nitrogen atoms as ring-constituting atoms).

Specific preferable examples of the compound include pyridine and lutidine.
(ii) A 4- to 7-membered ($C_3$-$C_6$) monocyclic nitrogen-containing non-aromatic heterocyclic compound optionally substituted with one or more alkyl groups (preferably, this heterocycle can contain 1 to 3 nitrogen atoms as ring-constituting atoms) (part or all of the substituents are substituted on the nitrogen atom(s)).

Specific preferable examples of the compound include piperidine.
(iii) Benzene optionally substituted with 1 or 2 —$NR_2$ groups (wherein R, in each occurrence, independently represents hydrogen or alkyl (preferably methyl)).

Specific preferable examples of the compound include aniline.
(iv) Triazine optionally substituted with 1 to 3 substituents selected from the group consisting of halogen atoms, hydroxyl, amino, and phenyl.
(v) Alkylamine.

Preferable examples of the compound include an alkylamine of the formula: $R_3N$ (wherein R, in each occurrence, independently represents $C_2$-$C_8$ primary alkyl or $C_3$-$C_7$ secondary alkyl);
an alkylamine of the formula: $R_2NH$ (wherein R, in each occurrence, independently represents $C_1$-$C_8$ primary alkyl, $C_3$-$C_7$ secondary alkyl, or $C_4$-$C_{10}$ tertiary alkyl); and an alkylamine of the formula: $RNH_2$ (wherein R represents $C_1$-$C_8$ primary alkyl, $C_3$-$C_7$ secondary alkyl, or $C_4$-$C_{10}$ tertiary alkyl).
(vi) Organic salt Preferable examples of the compound include an organic salt of $R_4NX$ (wherein R represents $C_1$-$C_8$ primary alkyl, and X represents halogen).

These may be used alone, or in a combination of two or more.

The amount of the "base" may be selected from a range from a catalytic amount to a large excess.

Specifically, the amount of the "base" is preferably 0.01 to 20 moles, and more preferably 0.1 to 20 moles, per mol of the carbonyl compound (II).

In the present invention, when an acid is used as the reaction solvent, and a metal, metal hydroxide, metal hydride, metal alkoxide, metal oxide, or organic base is used as the base, it is obviously possible that the acid and the base undergo a reaction to form a metal salt or organic base salt of the acid.

The "salt" may be a compound formed by the reaction of an acid and a base. Examples mainly include a compound formed by the reaction of the acid and the base mentioned above as examples.

Examples of the "salt" include metal salts or ammonium salts of sulfuric acid or sulfonic acid (e.g., sodium sulfate, sodium hydrogensulfate, potassium sulfate, potassium hydrogensulfate, lithium sulfate, cesium sulfate, calcium sulfate, magnesium sulfate, ammonium sulfate, triethylammonium sulfate, pyridinium sulfate, trimethylpyridinium sulfate, polyarylammonium sulfate, polyvinylpyridinium sulfate, sodium methanesulfonate, ammonium methanesulfonate, tetramethylammonium methanesulfonate, potassium ethanesulfonate, lithium butanesulfonate, sodium benzenesulfonate, sodium toluenesulfonate, sodium trifluoromethanesulfonate, sodium polystyrenesulfonate);
metal salts or ammonium salts of carboxylic acids (e.g., sodium formate, ammonium formate, sodium acetate, potassium acetate, lithium acetate, magnesium acetate, calcium acetate, ammonium acetate, methylammonium acetate, diethylammonium acetate, triethylammonium acetate, tetraethylammonium acetate, pyridinium acetate, sodium propionate, potassium propionate, sodium butyrate, polyarylammonium acetate, polyvinylpyridinium acetate, sodium isobutyrate, sodium valerianate, sodium nonanoate, sodium chloroacetate, sodium bromoacetate, sodium trichloroacetate, sodium trifluoroacetate, sodium glycolate, sodium lactate, sodium benzoate, sodium oxalate, sodium succinate, sodium polyacrylate); inorganic metal salts (e.g., LiBr, LiI, NaBr, NaI, KBr, KI, RbBr, RbI, CsBr, CsI, BeBr$_2$, BeI$_2$, MgBr$_2$, MgI$_2$, CaBr$_2$, CaI$_2$, SrBr$_2$, SrI$_2$, BaBr$_2$, BaI$_2$, ZnBr$_2$, ZnI$_2$, CuBr$_2$, CuI$_2$, CuBr, CuI, AgBr, AgI, AuBr, AuI, NiBr$_2$, NiI$_2$, PdBr$_2$, PdI$_2$, PtBr$_2$, PtI$_2$, CoBr$_2$, CoI$_2$, FeBr$_2$, FeBr$_3$, FeI$_2$, FeI$_3$, MnBr$_2$, MnI$_2$, CrBr$_2$, CrI$_2$, PbBr$_2$, PbI$_2$, SnBr$_2$, SnI$_2$, SnBr$_4$, SnI$_4$);

pyridinium salts or ammonium salts (e.g., NH$_4$Br, NH$_4$I, MeNH$_3$Br, MeNH$_3$I, Me$_4$NBr, Me$_4$NI, Et$_4$NBr, Et$_4$NI, Bu$_4$NBr, Bu$_4$NI, PhMe$_3$NBr, PhMe$_3$NI, PhCH$_2$NMe$_3$I, pyridinium bromide, pyridinium iodide, chloropyridinium iodide, methylpyridinium iodide, cyanopyridinium iodide, bipyridinium iodide, quinolium iodide, isoquinolium iodide, N-methylpyridinium bromide, N-methylpyridinium iodide, N-methylquinolium iodide);

phosphonium salts (e.g., Me$_4$PBr, Me$_4$PI, Et$_4$PI, Pr$_4$I, Bu$_4$PBr, Bu$_4$PI, Ph$_4$PBr, Ph$_4$PI);

metal salts or amine salts of hydrogen halides, hypohalous acids, halous acids, halogen acids, or perhalogen acids (e.g., sodium fluoride, potassium fluoride, cesium fluoride, ammonium fluoride, tetraethylammonium fluoride, tetrabutylammonium fluoride, polyarylammonium fluoride, sodium chloride, ammonium chloride, sodium hypochlorite, sodium chlorite, sodium chlorate, sodium perchlorate, sodium perbromate, sodium periodate); carbonates (e.g., sodium carbonate, potassium carbonate, lithium carbonate, sodium hydrogencarbonate, potassium hydrogencarbonate, lithium hydrogencarbonate, calcium carbonate, magnesium carbonate);

metal salts or amine salts of phosphoric acids (e.g., sodium phosphate, potassium phosphate, sodium hydrogenphosphate, sodium dihydrogenphosphate, ammonium phosphate, pyridinium phosphate);

metal salts or amine salts of nitric acid (e.g., sodium nitrate, potassium nitrate, ammonium nitrate, pyridinium nitrate); metal salts or amine salts formed of Lewis acids and hydrogen halides (e.g., NaBF$_4$, KBF$_4$, LiBF$_4$, NaSbF$_6$, NaAsF$_6$, NaPF$_6$, NH$_4$BF$_4$, NH$_4$SbF$_6$, NH$_4$PF$_6$);

phosphonium salts (e.g., tetramethylphosphonium fluoride, tetramethylphosphonium acetate, tetraphenylphosphonium fluoride); and room-temperature molten salts having fluoride anions or HF (e.g., (C$_2$H$_5$)$_4$NF, 1-ethyl-3-methylimidazolium fluoride, (C$_2$H$_5$)$_3$N—(HF)$_n$, (C$_2$H$_5$)$_4$NF—(HF)$_n$, (n-C$_4$H$_9$)$_3$N—(HF)$_n$, (n-C$_4$H$_9$)$_F$NF—(HF)$_n$, BF$_3$.Et$_2$O—(HF)$_n$ (wherein n=1 to 20)).

These may be used alone, or in a combination of two or more.

Examples of the "additive" include halogens, interhalogen compounds, and polyhalides.

Examples of the "halogens" include iodine, bromine, and chlorine, as described above. Of these, iodine and bromine are preferable, and iodine is more preferable.

Examples of the "interhalogen compounds" include ClF, BrF, ICl, IBr, I$_2$Cl$_6$, and IC$_{13}$.

Examples of the "polyhalides" include LiCl$_4$I, NaCl$_4$I, KCl$_4$I, CsCl$_4$I, RbCl$_4$I, Me$_4$NCl$_4$I, Et$_4$NCl$_4$I, Pr$_4$NCl$_4$I, Bu$_4$NCl$_4$I, PhNMe$_3$Cl$_4$I, PhCH$_2$NMe$_3$Cl$_4$I, Me$_3$SCl$_4$I, Cl$_8$IP, KCl$_3$I$_2$, Me$_4$NCl$_3$I$_2$, 2,2'-bipyridinium μ-chlorodichlorodiiodate, 2,2'-biquinolinium μ-chlorodichlorodiiodate, KCl$_2$I, Me$_4$NCl$_2$I, Me$_4$NClI$_2$, Et$_4$NCl$_3$, Ph$_4$AsCl$_3$, KClF$_2$, Me$_4$NClF$_4$, CsClF$_4$, CsCl$_3$FI, KBrClI, NH$_4$BrClI, Me$_4$NBrClI, Me$_4$NBrCl$_2$, Bu$_4$NBrCl$_2$, Me$_4$NBrCl$_2$I$_2$, CsBrFI, NaBrF$_2$, KBrF$_2$, CsBrF$_4$, Me$_4$NBrF$_4$, CsBrF$_6$, Me$_4$NBrF$_6$, Et$_4$NBr$_6$Cl, CsBr$_3$, Me$_4$NBr$_3$, Et$_4$Br$_3$, Bu$_4$NBr$_3$, PhCH$_2$NMe$_3$Br$_3$, pyridinium tribromide, Br$_7$P, CsBrI$_2$, Me$_4$NBrI$_2$, Me$_4$NBrI$_4$, Me$_4$NBrI$_6$, KBr$_2$Cl, Me$_4$NBr$_2$Cl, Bu$_4$NBr$_2$Cl, KBr$_2$I, Me$_4$NBr$_2$I, Bu$_4$NBr$_2$I, 2,2'-bipyridinium μ-bromodibromodiiodate, NaF$_2$I, KF$_2$I, CsF$_4$I, CsF$_6$I, CsF$_8$I, KI$_3$, CsI$_3$, Me$_4$NI$_3$, Et$_4$NI$_3$, Pr$_4$NI$_3$, Bu$_4$NI$_3$, pyridinium triiodide, Me$_4$NI$_{45}$, Et$_4$NI$_7$, Me$_4$NI$_9$, Me$_4$PBr$_3$, Me$_4$PI$_3$, Me$_4$PIBr$_2$, Me$_4$PICl$_2$, Et$_4$PI$_3$, Bu$_4$PI$_3$, Ph$_4$PI$_3$, Ph$_4$PBr$_3$, and Ph$_4$PIBr$_2$.

These additives may be used alone, or in a combination of two or more.

As described above, when IF$_5$ is used in combination with at least one member selected from the group consisting of acids, bases, salts, and additives, preferably 1 to 3 members selected from the group thereof (more preferably 1 to 3 members selected from the group thereof, excluding combinations of an acid, a base, and a salt), the combination may be in the form of a complex.

Examples of the complex include an IF$_5$—HF-pyridine complex.

In step A, IF$_5$ is preferably used in an amount of 0.2 to 20 moles, more preferably 0.3 to 5 moles, and still more preferably 0.4 to 2 moles, per mol of the carbonyl compound (II), which is a substrate.

In step A, the additive is preferably used in an amount of 0.1 to 10 moles per mol of the carbonyl compound (II).

The reaction temperature of step A is preferably −70 to 200° C., and more preferably −20 to 100° C.

Step A can be carried out in the presence or absence of a reaction solvent.

Examples of the reaction solvent include aliphatic solvents, such as pentane, hexane, heptane, cyclohexane, and petroleum ether;

halogenated-aliphatic solvents, such as dichloromethane, dichloroethane, chloroform, fluorotrichloromethane, 1,1,2-trichlorotrifluoroethane, 2-chloro-1,2-dibromo-1,1,2-trifluoroethane, 1,2-dibromohexafluoropropane, 1,2-dibromotetrafluoroethane, 1,1-difluorotetrachloroethane, 1,2-difluorotetrachloroethane, heptafluoro-2,3,3-trichlorobutane, 1,1,1,3-tetrachlorotetrafluoropropane, 1,1,1-trichloropentafluoropropane, 1,1,1-trichlorotrifluoroethane, and polychlorotrifluoroethylene;

ester solvents, such as methyl formate, ethyl formate, methyl acetate, ethyl acetate, propyl acetate, methyl propionate, γ-butyrolactone, and propylene carbonate;

nitrile solvents, such as acetonitrile and propionitrile; aromatic solvents, such as benzene, chlorobenzene, toluene, dichlorobenzene, fluorobenzene, and nitrobenzene; ether solvents, such as diethyl ether, dipropyl ether, and tetrahydrofuran; and other solvents, such as N,N-dimethylformamide (DMF), dimethylsulfoxide (DMSO), water, nitromethane, N,N-diethylformamide, N,N-dimethylacetamide, 1-methyl-2-pyrrolidone, 1,3-dimethyl-2-imidazolidinone (DMI), tetramethyl urea, 1,3-dimethylpropylene urea, and hexamethylphosphoramide (HMPA).

These may be used alone, or in any combination of two or more.

The carbonyl compound (II) and IF$_5$, and optionally an acid, a base, a salt, and an additive can be added to the reaction system of step A in any order, as long as there is no long time interval.

As a post-treatment after the reaction of step A, a reducing agent may be added in order to reduce an overly oxidized organic compound (i.e., a by-product), or to reduce an excess of residual IF$_5$ or an oxidative compound from IF$_5$.

The reducing agent may be any compound having a reducing property.

Examples include inorganic or organic reducing agents, such as zinc powder, tin, tin chloride, iron, aluminum, sodium thiosulfate, butyltin hydride, sodium borohydride, and lithium aluminum hydride.

These may be used alone, or in a combination of two or more.

Step A above may comprise step A1 of reacting $IF_5$ with the disulfide compound (III), and step A2 of reacting the carbonyl compound (II) with the reaction product of step A1.

Step A1 and step A2 can be performed sequentially or simultaneously.

The reaction temperature of step A1 is preferably room temperature.

The upper limit of the reaction temperature of step A1 is preferably 100° C., and more preferably 70° C.

The lower limit of the reaction temperature of step A1 is preferably −50° C., more preferably −30° C., and still more preferably −20° C.

The reaction temperature of step A1 is preferably −20 to 100° C., and more preferably 0 to 70° C.

An excessively low reaction temperature may cause insufficient reaction of step A1.

An excessively high reaction temperature is disadvantageous in view of cost, and may cause an undesirable reaction.

Step A1 can be carried out in the presence or absence of a reaction solvent.

Specific examples of the reaction solvent include dichloromethane, tetrachloroethane, chloroform, carbon tetrachloride, cyclohexane, and mixed solvents of two or more of these.

The reaction product obtained in step A1 may be separated or purified, as desired, by using a conventional method, such as extraction, before subjecting the reaction product to step A2. Alternatively, the reaction product obtained in step A1 may be suitably used directly in step A2.

The upper limit of the reaction time of step A1 is preferably 72 hours, more preferably 48 hours, still more preferably 24 hours, even more preferably 12 hours, and particularly preferably 5 hours.

The lower limit of the reaction time of step A1 is preferably 1 minute, more preferably 10 minutes, and still more preferably 30 minutes.

The reaction time of step A1 is preferably 1 minute to 24 hours, more preferably 10 minutes to 12 hours, and still more preferably 30 minutes to 5 hours.

An excessively short reaction time may cause insufficient reaction of step A1.

An excessively long reaction time is disadvantageous in view of cost, and may cause an undesirable reaction.

The reaction temperature of step A2 is preferably room temperature.

The upper limit of the reaction temperature of step A2 is preferably 100° C., more preferably 70° C., still more preferably 50° C., even more preferably 30° C., particularly preferably 10° C., and particularly preferably 5° C.

The lower limit of the reaction temperature of step A2 is preferably −20° C., more preferably −10° C., still more preferably −5° C., and even more preferably −2° C.

The reaction temperature of step A2 is preferably −20° C. to 100° C., more preferably −20° C. to 70° C., still more preferably −10° C. to 20° C., even more preferably −5° C. to 10° C., and particularly preferably −5° C. to 5° C.

An excessively low reaction temperature may cause insufficient reaction of step A2.

An excessively high reaction temperature is disadvantageous in view of cost, and may cause an undesirable reaction.

Step A2 may be carried out in the presence or absence of a reaction solvent.

Specific examples of the reaction solvent include dichloromethane, tetrachloroethane, chloroform, carbon tetrachloride, cyclohexane, and mixed solvents of two or more of these.

The upper limit of the reaction time of step A2 is preferably 48 hours, more preferably 24 hours, even more preferably 10 hours, and still even more preferably 5 hours.

The lower limit of the reaction time of step A2 is preferably 5 minute, more preferably 30 minutes, and still more preferably 1 hour.

The reaction time of step A2 is preferably 5 minutes to 48 hours, more preferably 30 minutes to 24 hours, still more preferably 1 hour to 10 hours, and even more preferably 1 to 5 hours.

An excessively short reaction time may cause insufficient reaction of step A2.

An excessively long reaction time is disadvantageous in view of cost, and may cause an undesirable reaction.

Step A1 and step A2 above may be performed in one pot.

In this embodiment, a complex formed of the base, the acid, and $IF_5$ can be used.

In one embodiment of the present invention, step A1 and step A2 are performed sequentially.

More specifically, the reaction of step A2 above can be initiated after the completion of the reaction of step A1 above.

In one embodiment of the present invention, step A1 and step A2 are performed simultaneously.

More specifically, the reaction of step A2 above can be initiated before the reaction of step A1 above is completed.

In this embodiment, a complex formed of the base, the acid, and $IF_5$ can be used.

The production method of the present invention can be conducted, for example, by placing a complex of the base, the acid, and $IF_5$, as well as the carbonyl compound (II), in a container, followed by addition of the disulfide compound (III) to the container.

The production method of the present invention may also be conducted, for example, by allowing the reaction of step A1 to proceed in a first container; and allowing the reaction of step A2 to proceed by placing the carbonyl compound (II) in a second container, and connecting the first container and the second container to allow the substances contained in these containers to be brought into contact with each other.

The difluoromethylene compound (I) produced by using the production method of the present invention can be purified, as desired, by a known method, such as extraction.

The conversion percentage of the production method of the present invention is preferably 50% or more, more preferably 70% or more, and still more preferably 90% or more.

According to the production method of the present invention, the difluoromethylene compound (I) is obtained in a yield of preferably 30% or more, more preferably 50% or more, and still more preferably 70% or more.

According to the production method of the present invention, the difluoromethylene compound (I) is obtained with a selectivity of preferably 50% or more, more preferably 60% or more, and still more preferably 70% or more.

EXAMPLES

The present invention is described below in more detail with reference to Examples. However, the present invention is not limited to these Examples.

Example 1

An $IF_5$—HF-pyridine complex (2.1 g, 6.6 mmol) was placed in a reactor (volume: 100 mL), to which 15 mL of dichloromethane was added, thus preparing a solution.

After this solution was cooled to 0° C., a solution of diphenyldisulfide (1.0 g, 4.6 mmol) in dichloromethane (8 mL) and benzaldehyde (0.97 g, 9.2 mmol) were added. The mixture was heated to room temperature, followed by stirring overnight.

After the reaction liquid was separated by filtration, a dichloromethane layer obtained by adding a saturated sodium hydrogen carbonate solution to the filtrate was separated. The solvent was distilled off, and FNMR analysis was performed to confirm the presence of $PhCHF_2$.

$^{19}$FNMR: δ-110.9 (d, 2F, J=60 Hz)

Example 2

An $IF_5$—HF-pyridine complex (0.90 g, 2.8 mmol) was placed in a reactor (volume: 100 mL), to which 3 mL of dichloromethane was added, thus preparing a solution.

After this solution was cooled to 0° C., a solution of bis(4-t-butyl-2,6-dimethylphenyl)disulfide (0.54 g, 1.4 mmol) in dichloromethane (6 mL) and benzaldehyde (0.58 g, 5.5 mmol) were added.

The mixture was heated to room temperature, followed by stirring overnight.

After the reaction liquid was separated by filtration, a dichloromethane layer obtained by adding a saturated sodium hydrogen carbonate solution to the filtrate was separated. The solvent was distilled off, and FMMR analysis was performed to confirm the presence of $PhCHF_2$.

$^{19}$FNMR: δ-110.9 (d, 2F, J=60 Hz)

The invention claimed is:

1. A method for producing a difluoromethylene compound (I) containing at least one —$CF_2$— moiety, the method comprising step A of reacting $IF_5$ and
   a disulfide compound (III) of the formula: $R^4$—S—S—$R^4$, wherein $R^4$, in each occurrence, independently represents aryl optionally having at least one substituent or alkyl optionally having at least one substituent, with
   a carbonyl compound (II) containing at least one —C(O)— moiety.

2. The production method according to claim 1, wherein
the difluoromethylene compound (I) is a difluoromethylene compound represented by formula (1):

$$R^{11}\text{—}C_2\text{—}R^{12} \quad (1),$$

wherein $R^{11}$ and $R^{12}$ are identical or different, and each represents
(a) an organic group optionally containing at least one —$CF_2$— moiety or
(b) fluorine, and
the carbonyl compound (II) is a carbonyl compound represented by formula (2):

$$R^{21}\text{—}C(O)\text{—}R^{22} \quad (2),$$

wherein $R^{21}$ and $R^{22}$ are identical or different, and each represents
(a) hydrogen,
(b) hydroxyl, or
(c) an organic group optionally containing at least one —CO— moiety, or $R^{21}$ and $R^{22}$, taken together with the adjacent —C(O)— moiety, may form a ring, with the proviso that
neither $R^{11}$ nor $R^{12}$, and neither $R^{21}$ nor $R^{22}$, is an organic group bonded via —O—.

3. The production method according to claim 1, wherein
the difluoromethylene compound (I) is a difluoromethylene compound represented by formula (1):

$$R^{11}\text{—}CF_2\text{—}R^{12} \quad (1),$$

wherein
$R^{11}$ represents $R^{21}$ or fluorine,
$R^{12}$ represents $R^{22}$ or fluorine,
$R^{21}$ and $R^{22}$ are identical or different, and each represents
(a) hydrogen,
(b) hydroxyl, or
(c) an organic group, or
$R^{21}$ and $R^{22}$, taken together with the adjacent —$CF_2$— moiety, may form a ring,
with the proviso that
(i) neither $R^{11}$ nor $R^{12}$ is hydroxyl, and
(ii) neither $R^{11}$ nor $R^{12}$, and neither $R^{21}$ nor $R^{22}$, is an organic group bonded via —O—, and the carbonyl compound (II) is a carbonyl compound represented by formula (2):

$$R^{21}\text{—}C(O)\text{—}R^{22} \quad (2),$$

wherein
the symbols in the formula are as defined above.

4. The production method according to claim 1, further comprising reacting at least one member selected from the group consisting of acids, salts, and additives in addition to $IF_5$.

5. The production method according to claim 1, further comprising reacting an acid and a base in addition to $IF_5$.

6. The production method according to claim 4, wherein the acid is hydrogen fluoride.

7. The production method according to claim 5, wherein the base is a 5-membered monocyclic nitrogen-containing aromatic heterocyclic compound optionally substituted with one or more alkyl groups.

8. The production method according to claim 1, wherein $R^4$, in each occurrence, independently represents aryl optionally having at least one substituent.

9. The production method according to claim 5, wherein the acid is hydrogen fluoride.

10. The production method according to claim 9, wherein the base is a 5-membered monocyclic nitrogen-containing aromatic heterocyclic compound optionally substituted with one or more alkyl groups.

* * * * *